US00PP24301P3

(12) United States Plant Patent
Lighty

(10) Patent No.: US PP24,301 P3
(45) Date of Patent: Mar. 11, 2014

(54) ***HYDRANGEA* PLANT NAMED 'ANNIE'S BLUE'**

(50) Latin Name: *Hydrangea serrata*
Varietal Denomination: Annie's Blue

(75) Inventor: Richard W. Lighty, West Chester, PA (US)

(73) Assignee: CP Delaware, Inc., Wilmington, DE (US)

( * ) Notice: Subject to any disclaimer, the term of this patent is extended or adjusted under 35 U.S.C. 154(b) by 50 days.

(21) Appl. No.: 13/507,367

(22) Filed: Jun. 22, 2012

(65) Prior Publication Data

US 2013/0347159 P1 Dec. 26, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Annette Para
(74) *Attorney, Agent, or Firm* — Buchanan Ingersoll & Rooney PC

(57) ABSTRACT

A new and distinct *Hydrangea serrata* plant is provided that was discovered as a newly found seedling in a cultivated area. Attractive large blue to mauve lacecap flowers are formed that tend to be more blue when grown in acidic soils and more mauve when grown in neutral to basic soils. Strong sturdy branches are formed. Delicate yellow-green foliage is displayed. The plant is more floriferous than the 'Blue Billow' cultivar (non-patented in the United States) and the foliage is smaller than that of such comparative cultivar. Winter hardiness to U.S.D.A. Zone No. 6b has been observed. The plant is well suited for providing attractive ornamentation in the landscape. The cut flowers also can be included in cut flower arrangements.

2 Drawing Sheets

Botanical/commercial classification: *Hydrangea serrata/ Hydrangea* Plant.

Varietal denomination: cv. Annie's Blue.

SUMMARY OF THE INVENTION

The new *Hydrangea* plant was discovered during the summer of 2005 as a newly found seedling from among a population of *Hydrangea serrata* plants growing in a cultivated area (i.e., in a garden setting near a residence at Pomroy, Pa., U.S.A). The seeds used to produce the population of *Hydrangea serrata* plants had been collected in South Korea and were of unknown parentage. The previously available 'Blue Billow' *Hydrangea* cultivar (non-patented in the United States) had been similarly derived from seeds collected in South Korea. The discoverer of the new plant of the present invention was attracted to a single plant of the new cultivar from among the population which displayed the distinctive combination of characteristics described hereafter. Had this new plant not been discovered and preserved it would have been lost to mankind.

It was found that the new *Hydrangea* cultivar of the present invention:

(a) displays in abundance attractive large blue to mauve lacecap flowers that tend to be more blue when grown in acidic soils and more mauve when grown in neutral to basic soils,
(b) displays attractive delicate yellow-green foliage,
(c) displays sturdy branches,
(d) is winter hardy to U.S.D.A. Hardiness Zone 6b, and
(e) is well suited for growing as attractive ornamentation in the landscape.

The new cultivar well meets the needs of the horticultural industry. It can be grown to advantage in gardens and throughout the landscape where distinctive ornamentation is desired. The attractive flowers also can be used to advantage in cut flower arrangements.

The new cultivar can be readily distinguished from previously available *Hydrangea* cultivars, including the 'Blue Billow' cultivar, in view of its distinctive combination of characteristics. More specifically, the new cultivar forms larger flower clusters, forms more delicate foliage, and is significantly more floriferous than the 'Blue Billow' cultivar. The blooming period of the new cultivar has been found to generally correspond to that of the 'Blue Billow' cultivar.

The attractive blossoms are formed during the second year after the stems elongate.

The new cultivar has been asexually reproduced at West Grove, Pa., U.S.A. by the rooting of softwood stem cuttings. The characteristics of the new cultivar are firmly fixed and are stable. The new cultivar has been demonstrated to asexually reproduce in a true-to-type manner when subsequent generations are observed.

The new cultivar has been named 'Annie's Blue'.

BRIEF DESCRIPTION OF THE PHOTOGRAPHS

Figure 1:
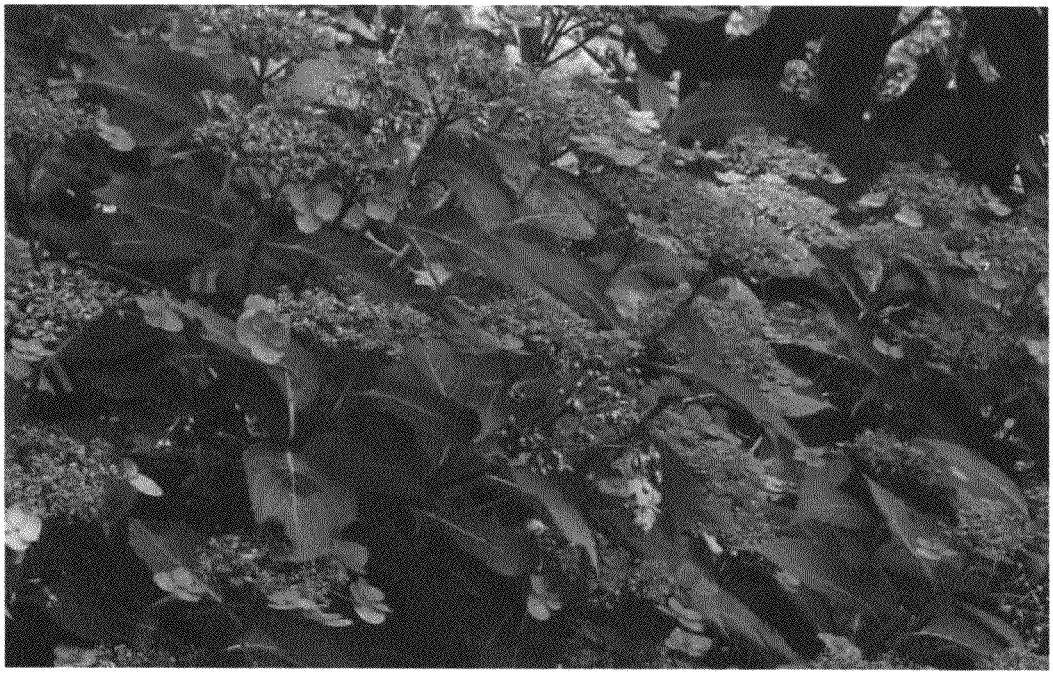
FIG. 1 illustrates the attractive large blue flowers and foliage of the new cultivar when grown in acidic soil. The photograph illustrates the original plant of the new variety during the summer of 2008 at an age of approximately three years while growing at Pomroy, Pa., U.S.A.
Figure 2:
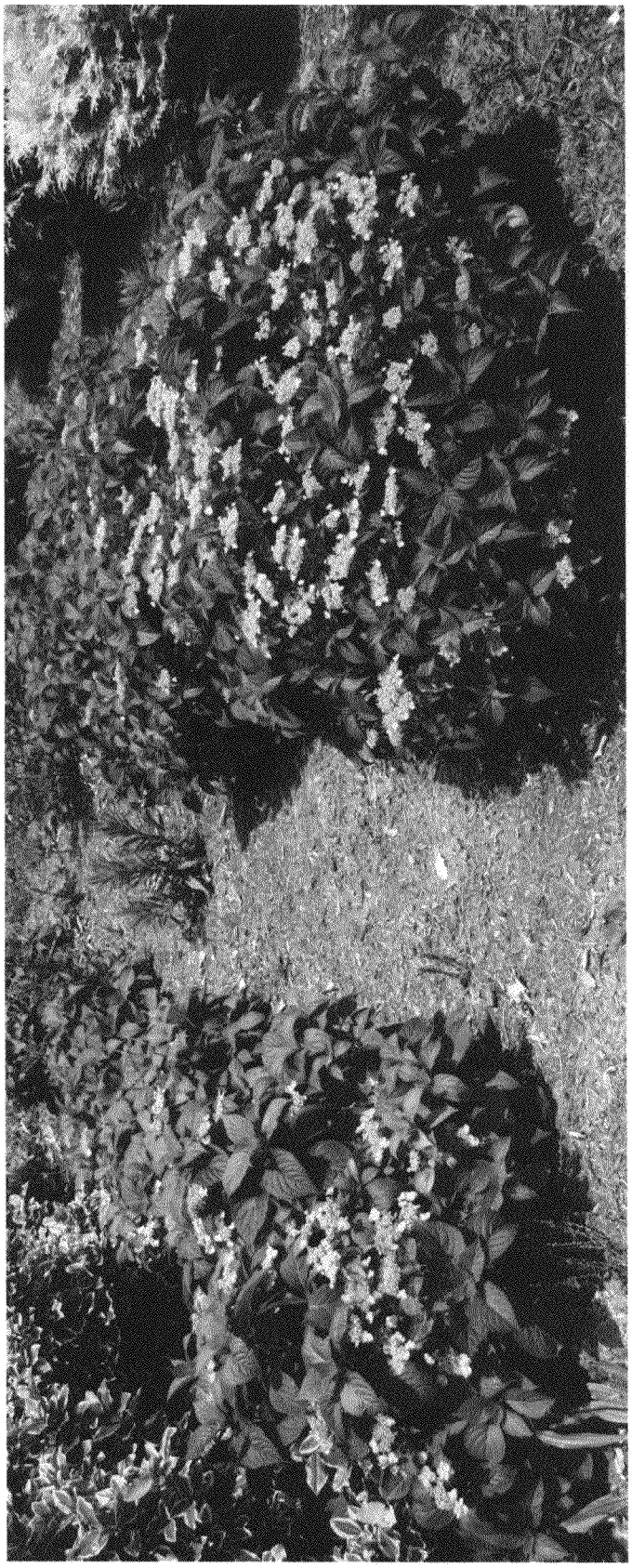
FIG. 2 illustrates for comparative purposes a typical flowering plant of the new cultivar when grown in neutral to basic soil on the right and a typical flowering plant of the 'Blue Billow' cultivar on the left, under the same growing conditions.

The plants had been asexually reproduced by the use of softwood cuttings and each plant was of approximately three years of age. The illustrated plants were growing in the ground under full sun on Jun. 14, 2012 at West Grove, Pa., U.S.A.

DETAILED DESCRIPTION

The following description is based on the observation of five-year-old plants of the new cultivar while being grown in neutral to basic soil in containers at West Grove, Pa., U.S.A. during May. Such plants had been asexually reproduced by the rooting of softwood stem cuttings. Reference to The R.H.S. Colour Chart (1995 Edition or equivalent) of The Royal Horticultural Society, London, England, is provided when a color is specifically designated. Common color terms are accorded their customary dictionary significance.

Botanical classification: *Hydrangea serrata.*

Origin: Newly found seedling in a cultivated area.

Plant:

- *Habit.*—Upright, bushy, broadly mounding deciduous shrub.
- *Height.*—Approximately 4 feet on average when mature.
- *Width.*—Approximately 5 feet on average when mature.
- *Growth habit.*—Rapid, vigorous grower.
- *Propagation.*—Softwood stem cuttings.
- *Root development.*—Takes approximately three weeks to fully develop roots when present as a liner in a 32-cell tray.
- *Time to produce.*—A flowering plant in a 1-gallon container can be produced in approximately 12 months following propagation.

Stems:

- *Length.*—Commonly approximately 21 cm on average to the base of the inflorescence.
- *Diameter.*—Commonly approximately 4.5 mm on average.
- *Stem shape.*—Substantially round.
- *Strength.*—Sturdy, and very strong.
- *Texture.*—Glabrous and slightly glossy.
- *Internode length.*—Approximately 7.1 cm on average.
- *Color.*—Yellow-Green Group 144A to Yellow-Green Group 144B.
- *Branching.*—A single dormant stem commonly produces 4 lateral stems on average. Pinching can be used to develop two sublateral stems on average.

Foliage:

- *Leaf division.*—Simple.
- *Configuration.*—Ovate to broadly ovate to elliptic.
- *Arrangement.*—Opposite.
- *Margin.*—Serrated.
- *Base.*—Obtuse.
- *Apex.*—Acute.
- *Length.*—Approximately 9.5 cm on average. This compares to a length of approximately 12 cm on average for the 'Blue Billow' cultivar.
- *Width.*—Approximately 5.5 cm on average. This compares to a width of approximately 6.5 cm on average for the 'Blue Billow' cultivar.
- *Number of leaves per stem.*—Commonly approximately 8 (4 pairs) per lateral stem on average.
- *Color.*—Upper surface: near Green Group 137A. Under surface: near Green Group 138B.
- *Venation.*—Penninerved, recessed on upper surface, near Yellow-Green Group 145A on the upper surface, and near Yellow-Green Group 145C on the under surface.
- *Texture.*—Glabrous on upper and under surfaces, and matte on the upper surface.
- *Attachment.*—Petiolate.
- *Petiole.*—Length: commonly approximately 7 cm on average. Width: commonly approximately 5 mm on average. Color: near Yellow-Green Group 144A.

Inflorescence in general:

- *Time.*—Early spring, typically for approximately three weeks from June to early July, at West Grove, Pa., U.S.A.
- *Type.*—Terminal compound globose corymb of rotate-shaped flowers.
- *Sterility.*—Commonly approximately 70 percent of the flowers are sterile.
- *Size.*—Commonly approximately 9.5 cm in diameter.
- *Number.*—Numerous, commonly approximately 143 sterile flowers and approximately 60 fertile flowers per inflorescence. This compares to a lesser flower total of approximately 45 for the 'Blue Billow' cultivar.
- *Stress.*—Moderate durability to stress.
- *Fragrance.*—None.
- *Bud length.*—Approximately 3 mm on average.
- *Bud width.*—Approximately 4 mm on average.
- *Bud opening time.*—Commonly approximately 5 days.
- *Bud color.*—Yellow-Green Group 145A overlaid with Red-Purple Group 73A.

Sterile inflorescence (neutral to basic soil):

- *Flower diameter.*—Approximately 5 cm.
- *Flower depth.*—Approximately 2.3 cm.
- *Color.*—Upper surface: near Red-Purple Group 63C blending to Red-Purple Group 63B towards the center. Under surface: near Red-Purple Group 63C.
- *Peduncles.*—Commonly approximately 1 cm in length, approximately 1 mm in width, generally smooth and covered with short fuzz, and Yellow-Green Group 145B in coloration.

Fertile inflorescence (neutral to basic soil):

- *Flower diameter.*—Approximately 1 cm.
- *Flower depth.*—Approximately 7 mm.
- *Petal number.*—5 on average.
- *Petal shape.*—Ovate.
- *Petal apex.*—Acute.
- *Petal base.*—Truncate.
- *Petal margin.*—Entire.
- *Petal color.*—Upper surface: when fully open near Red-Purple Group 70C blending to Red-Purple Group 70B at the base. Under surface: when fully open near Red-Purple Group 65C.
- *Stigma.*—Number: 3. Diameter: less than 1 mm. Color: near Yellow-White Group 158B.
- *Styles.*—Width less than 1 mm.
- *Anther.*—Number: approximately 10 on average. Shape: bi-lobed. Diameter: less than 1 mm. Color: near White Group 155A.
- *Filaments.*—Length: approximately 5 mm on average. Width: less than 1 mm. Color: commonly approximately five are Violet-Blue Group 95C, and approximately five are Purple Group 77D.
- *Fruit and seeds.*—None observed during observations to date.

*Peduncles.*—Commonly approximately 1 cm in length, approximately 1 mm in width, generally smooth and covered with short fuzz, and Yellow-Green Group 145B in coloration.

*Sepals.*—Number: 5 on fertile flowers. Arrangement: rotate. Texture: generally smooth. Apex: acute. Margin: entire.

Development:

*Disease tolerance.*—No particular susceptibility to disease has been encountered during observations to date.

*Cold hardiness.*—Has performed well to U.S.D.A. Hardiness Zone No. 6b during observations to date.

*Culture.*—Plant in moist, humus-rich, well-drained soil. Alkalinity/acidity influences flower color as indicated.

Plants of the 'Annie's Blue' cultivar have not been observed under all possible environmental conditions to date. Accordingly, it is possible that the phenotypic expression may further vary somewhat with changes in light intensity and duration, cultural practices, and other environmental conditions.

I claim:

1. A new distinct *Hydrangea serrata* plant that displays the following combination of characteristics:

(a) displays in abundance attractive large blue to mauve lacecap flowers that tend to be more blue when grown in acidic soils and more mauve when grown in neutral to basic soils, (b) displays attractive delicate yellow-green foliage, (c) displays sturdy branches, (d) is winter hardy to U.S.D.A. Hardiness Zone 6b, and (e) is well suited for growing as attractive ornamentation in the landscape;

substantially as illustrated and described.

* * * * *